United States Patent
Portney

(10) Patent No.: US 8,668,333 B2
(45) Date of Patent: Mar. 11, 2014

(54) CONTRA-ASPHERIC TORIC OPHTHALMIC LENS

(76) Inventor: Valdemar Portney, Newport Coast, CA (US)

( * ) Notice: Subject to any disclaimer, the term of this patent is extended or adjusted under 35 U.S.C. 154(b) by 141 days.

(21) Appl. No.: 13/312,529

(22) Filed: Dec. 6, 2011

(65) Prior Publication Data

US 2012/0147321 A1 Jun. 14, 2012

Related U.S. Application Data

(60) Provisional application No. 61/421,100, filed on Dec. 8, 2010, provisional application No. 61/426,201, filed on Dec. 22, 2010, provisional application No. 61/492,251, filed on Jun. 1, 2011.

(51) Int. Cl.
*G02C 7/04* (2006.01)
*A61F 2/16* (2006.01)

(52) U.S. Cl.
USPC ..................... 351/159.38; 623/6.23

(58) Field of Classification Search
USPC .............. 351/159.21, 159.38; 623/6.23, 6.24, 623/6.27–6.29
See application file for complete search history.

(56) References Cited

U.S. PATENT DOCUMENTS

| 5,570,143 | A | 10/1996 | Newman |
| 5,796,462 | A | 8/1998 | Roffman et al. |
| 6,537,545 | B1 * | 3/2003 | Karageozian et al. ........ 424/94.4 |
| 2004/0106992 | A1 * | 6/2004 | Lang et al. ................... 623/6.28 |
| 2010/0315589 | A1 | 12/2010 | Portney |

\* cited by examiner

*Primary Examiner* — Darryl J Collins
(74) *Attorney, Agent, or Firm* — Hacker Daghighian & Martino

(57) ABSTRACT

An ophthalmic toric lens to be worn on an eye or implanted inside of an eye, the lens includes an anterior surface, a posterior surface, and a toric shape formed into one of the anterior and posterior surfaces, the toric shape comprising two non-spherical principle meridians each having a region within an annular area of optical zone and the region of one principle meridian being configured for producing a longitudinal ray aberration of a different sign than a longitudinal ray aberration sign from the region of another principle meridian.

6 Claims, 5 Drawing Sheets

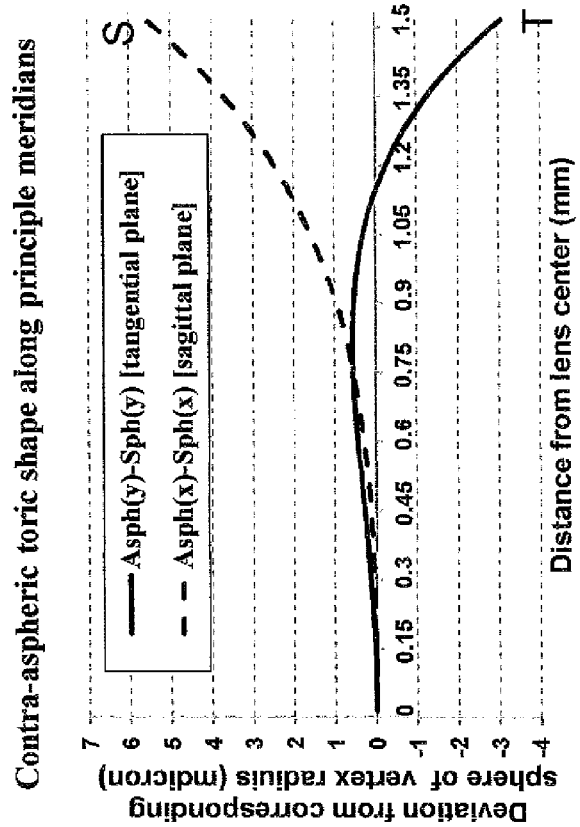
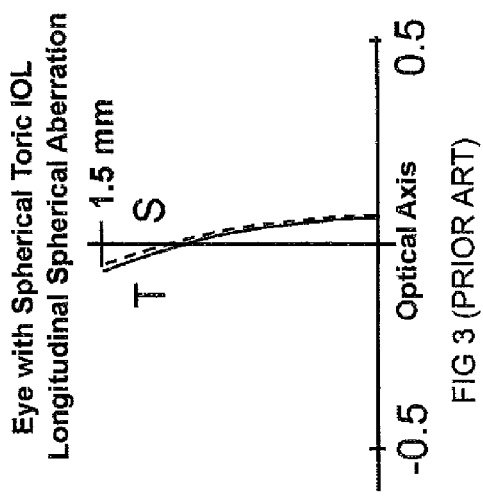
FIG 3 (PRIOR ART)
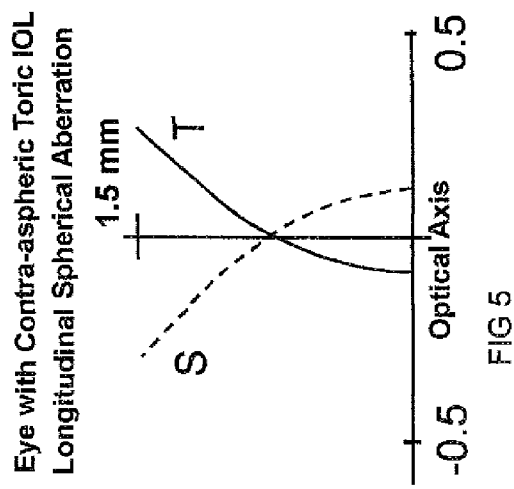
FIG 5

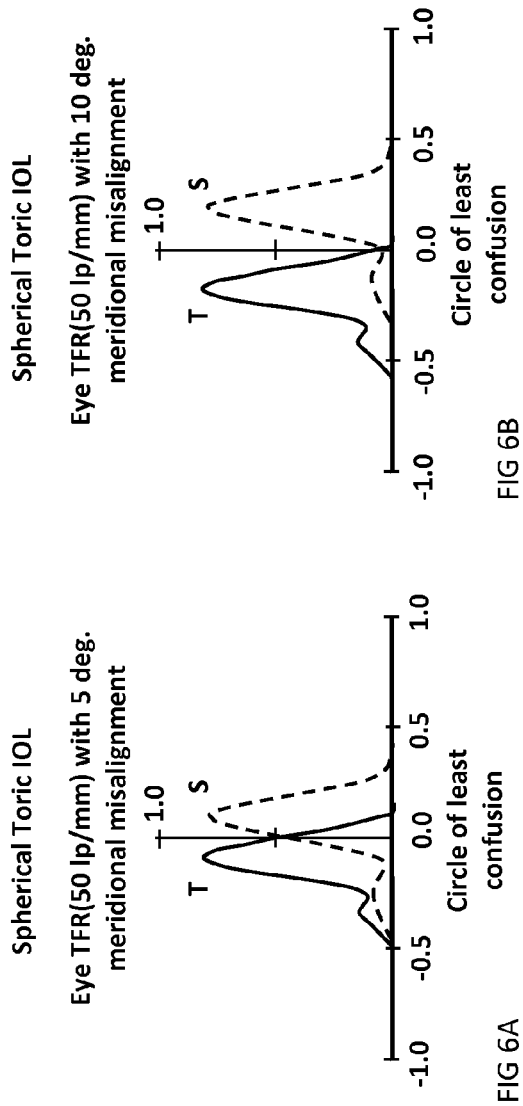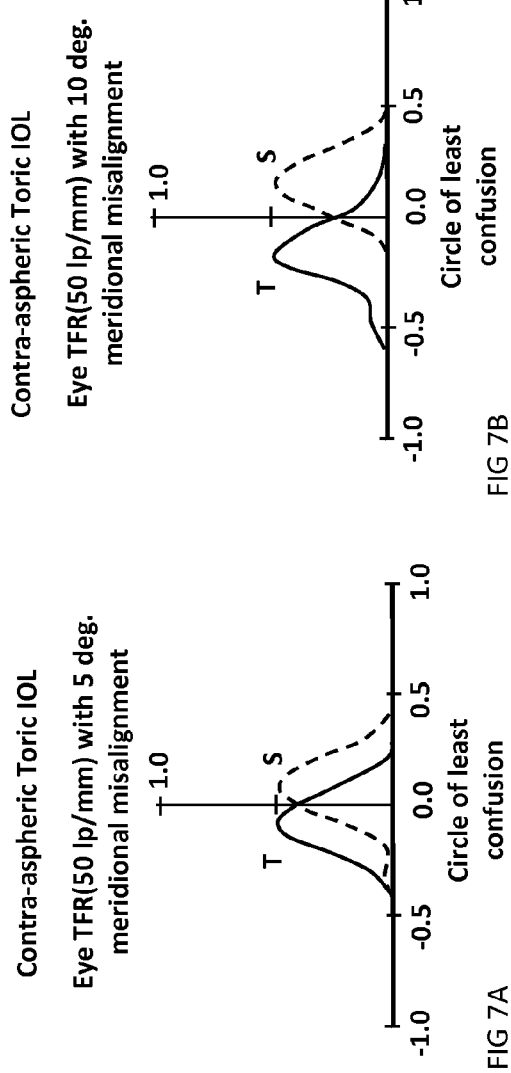

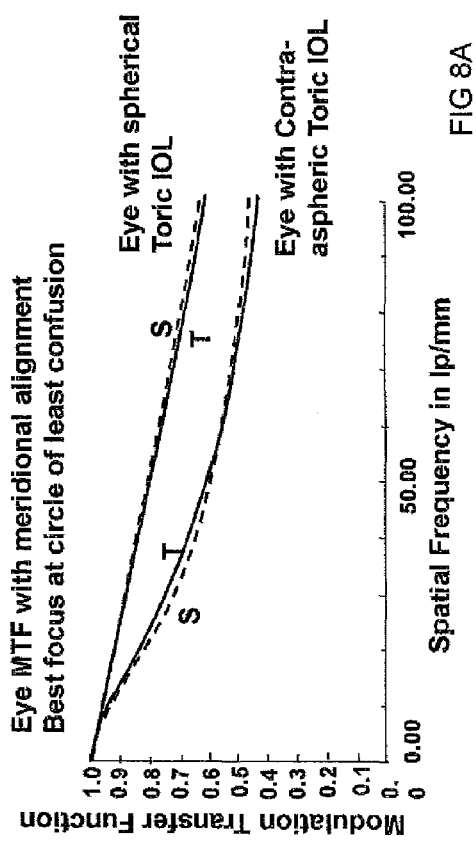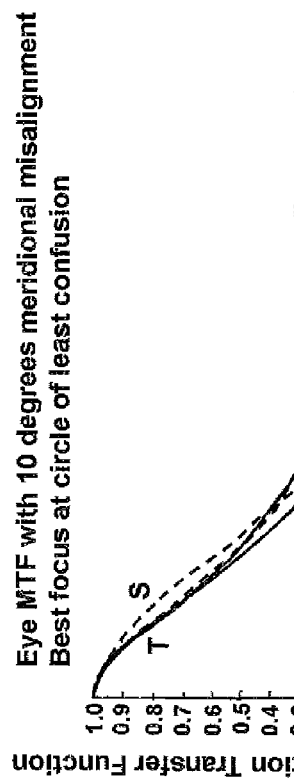

CONTRA-ASPHERIC TORIC OPHTHALMIC LENS

The present application claims priority from U.S. Provisional Application Ser. No. 61/421,400 filed Dec. 8, 2010; Ser. No. 61/426,201 filed Dec. 22, 2010; and Ser. No. 61/492,251 filed Jun. 1, 2011. These applications are to be incorporated into the present application in their entirety.

FIELD OF THE INVENTION

The present invention relates to toric ophthalmic lenses which provide cylinder power to correct for astigmatism refractive error.

BACKGROUND OF THE INVENTION

Astigmatism discussed in this invention disclosure is an astigmatism formed at the optical axis when the optical system is not rotationally symmetric about the optical axis. This is usually due to a toroidal shape of at least one of the ocular surfaces of the eye, most commonly the anterior corneal surface. This type of ocular astigmatism is called corneal astigmatism. Toroidal shape is two-curvature shape described by a surface with meridians of steepest and flattest curvatures located at right angle to each other. These meridians and principle meridians. A difference between the curvatures in terms of dioptric power is also called cylinder power of the toric lens. The described type of ocular astigmatism is also called regular astigmatism which is correctable by an optical aid such as spectacles, contact lens, corneal implant or intraocular lens.

Ocular astigmatism may also be due to an ocular surface of the eye is transversely displaced or tilted, most commonly a surface of crystalline lens in phakic subjects. This type of astigmatism is called lenticular astigmatism. Lenticular astigmatism almost invariably manifests the flattest meridian close to vertical orientation and usually does not exceed 1.5 D cylinder. Corneal astigmatism on the other hand, manifests large variation in the meridian orientation and magnitude.

Astigmatism correction commonly involves correction for other ocular deficiencies such as myopia (nearsightedness), hyperopia (farsightedness), aphakic and presbyopia, and the corrective toric ophthalmic lens may include spherical corrective power and multifocal corrective power for the corresponding ocular deficiency correction.

The astigmatism correction requires proper toric lens orientation—the lens flattest meridian to be aligned with the steepest meridian of the cornea, or steepest meridian of the eye refraction error if lenticular astigmatism is involved. The toric lens alignment in reference to ocular astigmatism meridian, so called rotational alignment or meridional alignment, is the most critical factor of a toric lens performance requirement in order to allow maintaining an acceptable image quality.

Eye's astigmatism that combines corneal and lenticular astigmatism comes into play for toric contact lens or phakic IOL applications, i.e. the IOL that compliments natural crystalline lens. Corneal astigmatism comes into play for toric aphakic IOL application. i.e. the IOL that replaced natural crystalline lens. This disclosure will reference below to astigmatism of eye as a general reference that includes either eye's astigmatism or corneal astigmatism and a reference to a toric lens includes either a toric contact lens or phakic IOL or aphakic IOL.

Thus, a toric lens is designed to compensate for a cylinder of the eye in the aligned position of its cylinder meridian with the eye's cylinder meridian and the lens toric cylinder magnitude is the same as eye's cylinder magnitude but they are of opposite sign. Assuming that in this condition the eye does not manifest any refractive error, i.e. both cylinder and spherical error are corrected. A meridional misalignment of a toric lens leads to a resultant cylinder. A resultant cylinder magnitude is proportional to both: eye's cylinder intended to be corrected by the toric lens and a magnitude of meridional misalignment angle, i.e. angle between toric axes of the lens and eye. A spherical error correction is not impacted by a misalignment, meaning if a spherical error was corrected in the aligned toric lens position, a toric lens meridional misalignment does not introduce a spherical error and only effect resultant cylinder.

The attempt to reduce sensitivity to toric lens meridional misalignment can be found in U.S. Pat. No. 5,570,143 by Newman where aspheric surface shape that induced a depth of focus was discussed. The lens according to Newman's invention includes optical topography on the surfaces of the lens which induces a depth of focus. When a lens meridians line up with the meridians the cylinder power requirement is fulfilled. If the meridians do not line up, i.e. a condition of meridional misalignment, the author speculates that the depth of focus corrects for the resulted overrefracton. The Newman's patent references to 1.5 D depth of focus as an example.

The Newman's patent relies on the assumption that an increase in depth of focus (depth of field) increases the width of each tangential and sagittal focal segments thus improving their overlap at the best image defined by the circle of least confusion and, therefore, image quality for the corresponding meridional misalignment as compared with a toric lens without a depth of focus increase. Conceptually it is correct but there are two fundamental issues with the Newman's patent: (a) an increase in depth of focus reduces the image quality and no specificity has been provided in the patent in this regards, and (2) depending upon the corresponding asphericity design a depth of focus might increase the overlap between tangential and sagittal focal segments, keep the same or even reduce it.

Another attempt to address meridional misalignment can be found in U.S. Pat. No. 5,796,462 by Roffman. The Roffman's patent describes asphericity application to each toric meridian in a form of a prolate aspheric curve. Similar to Newman's disclosure, the patent relies on the increased depth of focus to reduce sensitivity to the meridional misalignment but also applying it to the toric surface in such a way that the effective cylinder decreases from the center of the lens towards the periphery of the optical zone. The issue with this approach is that the described aspherization leaves residual cylinder even with lens perfect meridional alignment. Similar to Newman's patent, the disclosure in based upon refraction scalar consideration in addressing meridional misalignment despite the fact that a system with a toric surface manifests vector characteristics. In addition, no disclosure of the particulars of the aspheric surface that increases a depth of focus with positive impact in the image quality has been disclosed.

In view of the prior arts limitations, there is a need for improvement of the toric ophthalmic lens design that reduces sensitivity to meridional misalignment.

SUMMARY OF THE INVENTION

Before explaining the invention, an explanation how toric lenses are analyzed is introduced.

Meridional alignment of the toric to correct eye astigmatism is the meridional alignment when steepest meridian called a principle meridian is aligned with flattest principle meridian of ocular toric surface, for instance anterior corneal surface, or flattest principle meridian is aligned with steepest principle meridian of the ocular toric surface. Because a regular astigmatism is considered, the other principle meridian is perpendicular to the one involved in the alignment and is aligned simultaneously. As a result, an ocular astigmatism or cylinder refraction error is null. Practically, a perfect meridional alignment is difficult to achieve and a meridional misalignment results in a resultant astigmatism or cylinder of a magnitude that is proportional to a magnitude of a meridional misalignment.

In order to understand how the resultant astigmatism is determine one has to introduce oblique power of a toric lens, i.e. a power at the meridian of angle θ from one of the principle meridian orientations. An optical design software such as Zemax or other analyze the image quality of an optical system at the tangential (vertical or y-axis) and sagittal (horizontal or x-axis) meridians and, therefore, the toric lens principle meridians orientation must be also oriented at the same axes. A oblique power of a toric lens at the angle θ is:

$$P_t(\theta) = S + C \cdot \cos^2(\theta - \alpha) \qquad \text{Eq. 1,}$$

where S=spherical power and C=cylinder power of the toric lens and α=inclination angle of a principle meridian.

The Eq. 1 can be defined also by "Sine" function instead of "Cosine" if another principle meridian is taken for the toric lens orientation.

The Eq. 1 can be rewritten in a simpler form to remove square of cosine function:

$$P_t(\theta) = S + \frac{c}{2} + \frac{c}{2} * \cos[2(\theta - \alpha)] \qquad \text{Eq. 2}$$
$$= M + \frac{c}{2} \cos[2(\theta - \alpha)],$$

where M=mean refractive error.

Thus, a toric lens is decomposed into spherical lens of power M and so called JCC lens (Jackson cross-cylinder) of power $$J_\alpha = \frac{c}{2}$$

with its axis inclined at the angle α. Double of the angle of the oblique astigmatism JCC in the Eq. 2 means that its rectangular components are at zero and 45 degrees axes instead of common axes at zero and 90 degrees and the corresponding components are called $J_0 = J_\alpha \cdot \cos(2\theta)$ as JCC power component at the axis of zero degree orientation and $J_{45} = J_\alpha \cdot \sin(2\theta)$ as JCC power component at the axis of 45 degree orientation. Thus, in order to calculate a resultant power of two toric lenses with meridional misalignment one has to combine their zero and 45 degree JCC components and then convert the resultant $J_{0r}$ and $J_{45r}$ back to the combined $J_r$: $J_r = \sqrt{J_{0r}^2 + J_{45r}^2}$. The axis of the resultant cylinder, $\alpha_r$, is determined by:

$$\tan(2\alpha_r) = \frac{J_{45r}}{J_{0r}}.$$

The result of the analysis of toric lenses with meridional misalignment indicated that in order for the resultant toric system to have its principle meridians in y-axis and x-axis ($\alpha_r$=90 or 0) for optical design software analysis, the orientations of the principle meridians of the corresponding toric lenses must be at the opposite angular distances from 45 degrees or 45+180=225 degrees in the opposite quadrant. For instance, to analyze image quality for 10 degrees of meridional misalignment between corneal toric lens and toric IOL designed to correct for the corneal astigmatism in the aligned orientation, one of the principle meridians of the corneal lens must be placed either at 40 or 50 degrees and the principle meridian of the toric IOL must be placed correspondingly either at 50 or 40 degrees to provide 10 degrees of meridional misalignment between the toric surfaces and also to have the resultant principle meridians at y-axis and x-axis to enable the analysis of the resultant tangential and sagittal images by the optical software.

A lens in accordance with the present invention consists of front (anterior) and back (posterior) optical surfaces.

A toric shape of the lens of the present invention is formed onto one of the anterior and posterior surfaces with the toric shape being defined by non-spherical principle meridians of different best fit curvatures. The annular area is placed over the toric shape to select certain region of each principle meridian located at the same distance from the lens optical center. The region shapes along each principle meridians are such that they produce the opposite signs of the eye longitudinal ray aberrations (LSA) at the principle meridians in accordance with the present invention. LSA is defined as a difference between focus position between the marginal light ray (peripheral ray at the pupil periphery) and paraxial light ray (central ray at the optic axis). A region LSA is defined as LSA for a selected lens region as foci difference between the external ray of the lens region (furthest ray from the lens center) and internal ray of the lens region (closest ray to the lens center). Thus, a region LSA of the region of one principle meridian produces LSA of opposite sign from the region LSA of the region of another principle meridian where both regions lie within an annular area within the optical zone of the toric surface. The terms used to describe the above aspherization of the principle meridians of the toric surface is contra-aspheric toric surface.

In case of a meridional misalignment, the resultant toric ocular system forms tangential focal segment and sagittal focal segment with the best image defined by the circle of least confusion is maintained at the retina. Larger meridional misalignment create larger resultant cylinder thus further increasing the size of circle of least confusion and reducing image quality. An increase the depth of focus of tangential focal segment and sagittal focal segment towards the location of the circle of least confusion at the retina, increases their overlap thus reduces an effective separation between tangential and sagittal focal segments which leads to the improvement of the image quality at the retina. The aspherization of a toric surface to produce the opposite signs of LSAs of the eye at the principle meridians of the resultant cylinder does just that.

The common condition of ocular optic operation is at around 3 mm pupil (photopic pupil size) and the manifestation of LSAs with the opposite sings shall be within this pupil in order to reduce sensitivity to meridional misalignment in photopic condition. For instance there is a substantial enough annular region of the lens within 3 mm diameter where the corresponding region LSAs at both principle meridians are of the opposite signs. A substantial region is about 0.5 mm width or larger which constitutes about one third of the 1.5 mm radius or larger.

In order to produce LSAs of different signs, the aspherization along one of the principle meridians of the toric surface must largely flatten towards the lens periphery within about 3 mm diameter and largely steepen along the other principle meridian also within about 3 mm diameter.

In order to improve image quality at large pupil which usually occurs at low light condition, region LSAs of the opposite signs should be within the lens outside of about 3 mm lens diameter. For instance there is a substantial enough annular region of the lens outside 3 mm diameter where the corresponding region LSAs at both principle meridians are of the opposite signs. A substantial region is about 0.5 mm width or larger which constitutes about half of the zone between 2.5 mm and 1.5 mm radii difference or larger.

A toric lens of the present invention may consist of a single optical element or multiple optical elements.

A toric ophthalmic lens of the present invention may also comprise of a non-toroidal multifocal or a toroidal multifocal diffractive surface that produces far and near foci by utilizing appropriate diffraction orders.

Toroidal or toric multifocal diffractive surface may rely on toric shape of the other non-multifocal contra-aspheric toric surface or contra-aspheric toric base surface of the multifocal diffractive surface itself. In later case all characteristics and description of a contra-aspheric toric surface are applied to the base surface of the multifocal diffractive surface.

There is a significant challenge is to create a toric surface data points that is also multifocal diffractive surface because of a mathematical complexity, i.e. to convert a non-multifocal toric surface into base surface of multifocal diffractive lens. A relatively simple method is proposed that allows a conversion of a toric non-multifocal surface data set into toric multifocal surface data set for a chosen multifocal design.

Aspheric toric surface is commonly defined by the following equation:

$$Z = \frac{C_x X^2 + C_y Y^2}{1 + \sqrt{1 - C_x^2 X^2 - C_y^2 Y^2}} + \sum A_i X^i + \sum B_i Y^i \quad \text{Eq. 3}$$

where Z-axis is surface sag and X- and Y-exes are along the principle meridians of the toric surface;

$$C_x = \frac{1}{R_x} \text{ and } C_y = \frac{1}{R_y}$$

are vertex curvatures defined by vertex radii $R_x$ and $R_y$, and $A_i$ and $B_i$ are aspheric coefficients of the toric surface along the principle meridians correspondently.

The method is demonstrated on the example of JFL file format of surface data set used by Optoform CNC lathe but it can also be applied to the files of different formats. A toric surface is defined in JFL format by a set of data points Z, X and W as following: "X±xx.xxxxxxxZ±zz.zzzzzzzW±ww.wwwwww". A centrally symmetrical surface component is specified by Z and X coordinates where Z-axis is along the lathe spindle and defines the surface sag and X-axis is perpendicular to Z-axis to define a distance to the lens center. The additional coordinate W is added to specify a cutting tool movement along Z-axis at each X data point with each rotation to produce a cylinder component of the toric surface.

In a toric surface per the Equation 3 where X- and Y-coordinates define principle meridians of the highest and lowers dioptric powers of the toric surface and the cutting tool moves within the sag difference between X- and Y-axes 4 times, once for each 90 degrees of a single rotation. The spacing of the X data points specifies a spiral that the cutting tool follows and is defined by the cutting feed rate relative to the spindle speed. This can be expressed as following:

$$X_{spacing} = \frac{FR}{RPM} * \left(\frac{\alpha_{spacing}}{360}\right) \quad \text{Eq. 4}$$

where the manufacturing specifications are defined as:
FR=Feed Rate (mm/min) is defined by tool-material interaction for an acceptable optical quality of the surface finish.
RPM=spindle Rotation Per Minute is also defined by tool-material interaction for an acceptable optical quality of the surface finish.
$X_{spacing}$=X-coordinate step (mm). Thus, X data points can be expressed as a set of $X=\{X_i\}$.
$\alpha_{spacing}$=angular $\alpha$ coordinate of meridional data spacing (degree) for each $X_{spacing}$ (mm) which is defined by the equipment capability. Thus, $\alpha$ data points can be expressed as a set of $\alpha_i=\{\alpha_j^i\}$, where j=1 to J are meridional data points per one $X_i$ step in X-coordinate.

Therefore, a cutting tool movement is defined by the number J of $\alpha_{spacing}$ during one spindle rotation that occurs per one $X_{spacing}$ to create a cylinder component of the toric surface.

In JFL format, Z(X,Y)-coordinate in terms of data points in 3D space are defined by a number of $X_{spacing}$ and $\alpha_{spacing}$ and then converted into Z(X)-coordinate and W-coordinate where Z(X)-coordinate is defined only by X-axis as centrally symmetrical component of the toric surface and $W=\{W_j^i\}$ is a data set as deviation of Z(X,Y) surface per the Eq. 3 from the centrally symmetrical surface Z(X) for the same data set $X=\{X_i\}$:

Toric "non-multifocal" Surface Data Set: $Z_T(i)=\{Z_{Ti}(X_i, W_j^i)\}$ Eq. 5

(1) First step of the method is to define a corresponding centrally symmetrical surface by defining the surface sag for one of the coordinates X of Y in the Eq. 3. The resulting centrally symmetrical surface will be converted to a required multifocal surface. A selection of either X- or Y-axis is based on a familiarity of the resultant asphericity Z(X) or Z(Y) that used for the corresponding multifocal design. Assuming that X-axis is selected in the Eq. 3 for the corresponding centrally symmetrical surface:

$$Z = \frac{C_x X^2}{1 + \sqrt{1 - C_x^2 X^2}} + \sum A_i X^i \quad \text{Eq. 6}$$

In general, X-axis in Z(X)-coordinate can be different from X-axis as one of the principle meridians and coincides with in any meridian between the principle meridians. For instance, it can be at 45 degrees to the principle meridian to have the cutting tool movement in plus/minus directions along Z-axis. It is recommended but not critical to have X selection to coincide with one of the principle meridians because the mathematical surface description would be provided in a simple form Z(X) derived directly from the Eq. 3.

The corresponding centrally symmetrical surface Z(X) can be called monofocal surface. The selection of one of the principle meridians for the monofocal surface is the matter of convenience and it also allows to use the same asphericity as the one included with the toric surface in the Eq. 3 for one of the principle meridians.

The corresponding monofocal surface is then represented by $Z_{Si}$ data set at the same $X_{spacing}$ as in the toric non-multifocal surface in the Eq. 5:

Monofocal Surface Data Set: $Z_S(i)=\{Z_{Si}(X_i)\}$      Eq. 7

(2) Thus, the toric non-multifocal lens is correlated with the monofocal lens with the toric surface is being replaced by the monofocal surface described by one of its principle meridians. In the second step the monofocal lens is correlated with the multifocal lens of a desirable multifocal diffractive design. The monofocal surface is defined two-dimensionally as $Z_S=Z_S(X)$ per the Equation 4 which is assumed to be the monofocal surface for far power. Its conversion to multifocal surface of a selected design $Z_M=Z_M(X)$ is well developed procedure. Monofocal surface serves as a base surface in diffractive multifocal surface for far power.

The central point of the method is to define each data point $Z_{Mi}$ of the resulted multifocal surface at the same $X_{spacing}$ of X-axis that is used for the corresponding toric non-multifocal and monofocal surfaces in the Eq. 5 and 7:

Multifocal Surface Data Set: $Z_M(i)=\{Z_{Mi}(X_i)\}$      Eq. 8

(3) As a result, we have three data sets of surface sags of three types of surfaces specified at the same steps $X_i$. This allows to apply a deviation of the multifocal surface from the corresponding monofocal surface to the data set of the toric non-multifocal surface. The use of a general aspheric shape for one of the toric principle meridian allows to extract only a multifocal component of the multifocal surface which then is added to the original toric non-multifocal surface.

For each $X_i$ step the following multifocal component is determined:

$\Delta_{Mi}=Z_{Mi}-Z_{Si}$      Eq. 9

This is a difference in Z-coordinate between multifocal and monofocal surface sags at each step $X_i$. The same multifocal component then is added to Z-coordinate of the original toric non-multifocal surface at the same step $X_i$.

$Z_{TMi}=Z_{Ti}+\Delta_{Mi}$      Eq. 10

Z-coordinates for the same $X_i$ and all meridional data points $\alpha_{spacing}$ corresponding to one rotation at $X_i$ step are adjusted by the same magnitude $\Delta_{Mi}$ per the Eq. 10. This allows also to avoid a transition from one diffractive groove to another in a middle of rotation within one X step in case of a diffractive multifocal surface.

The resulted data set represents a toric multifocal surface with the same multifocal design as in the Eq. 8:

Toric Multifocal Surface Data Set: $Z_{TM}(i)=\{Z_{TMi}(X_i, W_j^i)\}$      Eq. 11 where the magnitudes $W_j^i$ are equivalent to the magnitudes $W_j^i$ in the Eq. 5 of the original toric non-multifocal surface to maintain the same cylinder component The cylinder component power is usually small as compared with spherical component power of the surface and the addition of the same multifocal component to the sags at both principle meridians should not affect the multifocal performance of the resulting toric multifocal surface. In addition, the format of the data set of the toric multifocal surface remains the same as in the original toric non-multifocal surface and can be used to produce the corresponding toric multifocal surface on the same equipment as the original toric surface.

A corresponding ophthalmic lens of this invention may be a contact lens, corneal implants or an intraocular lens that may be phakic or aphakic lens or a lens for treating refractive error after an IOL implantation (secondary IOL) or a lens for treating presbiopia (presbyopic lens). It may consists of a single and multiple optical elements.

The unexpected outcome of the present invention is that if a toric ophthalmic optic produces eye's longitudinal ray aberrations of different signs within 3 mm diameter between y- and x-axes when the axes coincide with the principle meridians of the toric surface, the resultant aspherization of the toric lens preserves an image quality with meridional misalignment to a larger degree than the equivalent toric lens without aspherization.

BRIEF DESCRIPTION OF THE FIGURES

FIG. 3 illustrates an example of longitudinal spherical aberrations at y- and x-axes within 3 mm diameter of nominal astigmatic eye with 2.5 D cylinder corrected by spherical toric lens.

FIG. 4 provides an example of contra-aspheric toric shape along the principle meridians of the toxic surface.

FIG. 5 illustrates an example of longitudinal spherical aberrations at y- and x-axes within 3 mm diameter of nominal astigmatic eye with 2.5 D cylinder corrected by contra-aspheric toric lens.

FIGS. 6A and 6B demonstrate depth-of-foci of resultant tangential and sagittal focal segments in the nominal astigmatic eye with 2.5 D cylinder at 5 and 10 degrees meridional misalignments of spherical toric lens.

FIGS. 7A and 7B demonstrate depth-of-foci of resultant tangential and sagittal focal segments in nominal astigmatic eye with 2.5 D cylinder at 5 and 10 degrees meridional misalignments of contra-aspheric toric lens with the toric surface described in the FIG. 4.

FIGS. 8A and 8B demonstrate the examples of Modulation Transfer Functions (MTFs) of nominal astigmatic eye with spherical toric lens and contra-aspheric toric lens with the toric surface per FIG. 4 in aligned condition and 10 degrees meridional misalignment condition at the position of the circle of least confusion.

DETAILED DESCRIPTION

Figure 1:
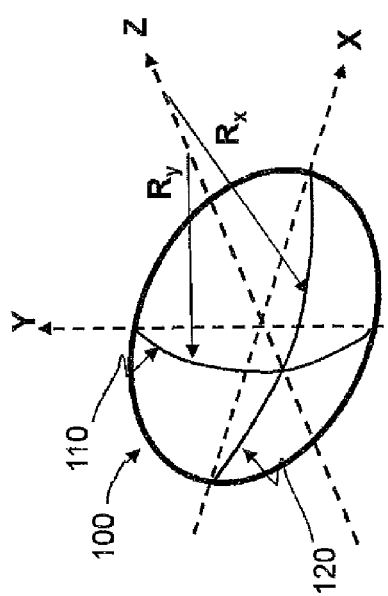
FIG. 1 illustrates a toric surface configuration.

FIG. 1 illustrates a toric surface configuration suitable for use as a contact lens, intraocular lens, single element lens or a multiple element lens. The optical axis coincides with Z-axis and the shortest radius $R_y$ (steepest curvature) is along y-axis that coincides with tangential meridian and the longest radius $R_x$ (flattest curvature) is along x-axis that coincides with sagittal meridian. The toric surface 100 is characterized by the principle meridians along the steepest curvature, 110, and flattest curvature, 120. In a spheric toric lens, $R_y$ and $R_x$ are constant along the corresponding principle meridians and the in an aspheric toric lens $R_y$ and $R_x$ are variable, that is, the toric surface has an aspheric cross section at the tangential or y-axis and sagittal meridians or x-axis of the described configuration commonly used for analysis by an optical design software such as Zemax for instance.

Toric surface Cylinder is defined by the difference in dioptric power between the meridians. The toric surface Spherical power is defined by the average dioptric power between the principle meridians.

Figure 2:
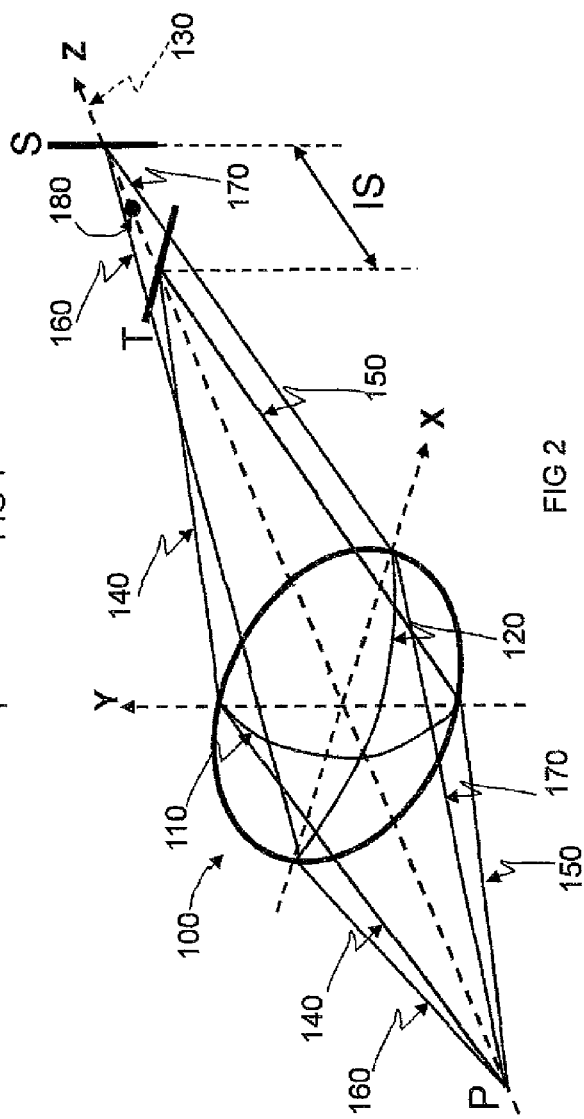
FIG. 2 illustrates ray tracing through a toric surface.

FIG. 2 illustrates ray tracing through a toric surface. The point object P is located on the optical axis 130. The transverse rays 140 and 150 are refracted by the toric surface 100 at the tangential meridian 110 to form tangential focal segment T. The sagittal rays 160 and 170 are refracted by the toric surface 100 at the sagittal meridian 120 to form sagittal focal segment S. The corresponding focal segments locate at different distances along the optic axis and are called the sagittal focus and the transverse focus, respectively. The distance between these foci is called interval of Sturm, IS. In between these two foci closely to the middle, a round but "blurry" image is formed. This is called the medial focus or "circle of least confusion", 180. This plane usually represents the best compromise image location in a system with astigmatism.

FIG. 3 illustrates an example of longitudinal spherical aberrations at y- and x-axes within 3 mm diameter of nominal astigmatic eye with 2.5 D cylinder corrected by spherical toric lens.

Both LSAs are practically equivalent and demonstrate a common LSA shape with a negative magnitude that is similar to the eye with a spherical lens of the same power as power of the spherical toric lens averaged between both principle meridians.

FIG. 4 provides an example of contra-aspheric toric shape along the principle meridians per the lens specification provided in the Table 1 below.

The curve characteristics along y-axis are designated by "y subscript" and along x-axis are designated by "x subscript" and both are plotted as the deviations from the corresponding spherical shapes defined by the vertex radii in y- and x-meridians.

Aspheric toric surface of a toric lens can be described by the following equations along y- and x-axes:

$$z(y) = \frac{c_y y^2}{1 + \sqrt{(1 - c_y^2 y^2)}} + A_{y2} y^2 + A_{y4} y^4 + \ldots$$

$$= \text{Sphere}(y^2) + A_{y4} y^4 + \ldots$$

$$z(x) = \frac{c_x x^2}{1 + \sqrt{(1 - c_x^2 x^2)}} + A_{x2} x^2 + A_{x4} x^4 + \ldots$$

$$= \text{Sphere}(x^2) + A_{y4} x^4 + \ldots$$

where "y" and "x" is the distance from the lens center along y-axis and x-axis correspondently, "$c_y$" and "$c_x$" are vertex curvatures along y- and x-axis correspondently, $c_y = 1/R_y$ and $c_x = 1/R_x$ with $R_y$ and $R_x$ being vertex radii along y- and x-axis correspondently. Coefficients $A_{y2}$, $A_{y4}$, etc are aspheric coefficients along y-axis and $A_{x2}$, $A_{x4}$, etc are aspheric coefficients along x-axis.

The term Sphere($y^2$) is the first taint defined by the sphere of the vertex radius $R_y$ shifted by the second term $A_{y2}$ and the term Sphere($x^2$) is defined correspondently along the x-axis. Aspherization along the principle meridians may change effective tangential and sagittal powers effective correction for conical cylinder and the second order aspheric confidents $A_{y2}$ and $A_{x2}$ play important role of adjusting the spherical powers of the principle meridians to maintain the correction for corneal cylinder.

Table 1 below lists the example of specifications of toric intraocular lens with toric aspheric surface according to the present invention.

TABLE 1

Eye specifications with astigmatic corneal lens 2.5 D Cylinder at spectacle plane and contra-aspheric IOL designed to correct for corneal astigmatism. Refractive indices: Cornea (1.377), aqueous (1.3374), IOL (1.489) and vitreous (1336).

| Parameters | y-axis | x-axis |
| --- | --- | --- |
| Front corneal principle meridional | | |
| radii (mm) | 7.8 | 8.238 |
| Corneal asphericity Q | −0.26 | −0.26 |
| Corneal thickness (mm) | 0.55 | 0.55 |
| Back corneal radius (mm) | 6.5 | 6.5 |
| Distant to pupil (mm) | 3.55 | 3.55 |
| Distance to front surface of IOL (mm) | 0.5 | 0.5 |
| Front toric principle meridional vertex | | |
| radii $R_y$ and $R_x$ (mm) | 9.55 | 7.839 |
| $A_{y2}$ and $A_{x2}$ | 0.0017963899 | −0.00058077593 |
| $A_{y4}$ and $A_{x4}$ | −0.0014042088 | 0.0008523824 |
| IOL thickness (mm) | 0.6 | 0.6 |
| Toric IOL back radius R (mm) | −30 (*) | −30 (*) |
| Distance to image plane (mm) | 18.38 | 18.38 |

(*) negative radius value for posterior convex surface

The astigmatic eye with spherical toric IOL had the same specifications as with contra-aspheric toric IOL except the absence of aspheric coefficients $A_{y2}$, $A_{x2}$, $A_{y4}$ and $A_{x4}$.

The FIG. 4 demonstrates that the aspherization largely flattens the surface along the tangential plane (y-axis) and largely steepens the surface along the sagittal plane (x-axis). The planes coincide with the principle meridians to demonstrate maximum and minimum curvatures.

FIG. 5 illustrates an example of longitudinal spherical aberrations at y- and x-axes within 3 mm diameter of nominal astigmatic eye with 2.5 D cylinder corrected by contra-aspheric toric lens.

The FIG. 5 demonstrates the result of aspherization on the longitudinal aberrations in y-axis and x-axis. In order to collect LSA in x-axis, the toric surfaces were rotated by 90 degrees because Zemax software plots LSA only in y-axis. The aspherization results in the LSAs of opposite signs for tangential (T) and sagittal (S) planes. This is the origin of the term used in describing aspherization of the present invention: "contra-aspherization" as being the reference to the opposite signs of the LSAs.

FIGS. 6A and 6B demonstrate depth-of-foci of resultant tangential and sagittal focal segments in the nominal astigmatic eye at 5 and 10 degrees meridional misalignments of spherical toric lens.

To analyze depth-of-focus and image quality at 5 degrees of meridional misalignment between corneal toric lens and toric IOL, one of the principle meridians of the corneal lens was placed at 42.5 degrees orientation and corresponding principle meridian of the toric IOL was placed at 47.5 degrees orientation. This lead for the resultant principle meridians of the astigmatic eye with toric IOL to be at y-axis and x-axis correspondently and enable to use Zemax optical design software to calculate Through Focus Responses (TFRs) at 50 lp/mm defining the depth-of-focus for the resultant tangential and sagittal images at 50 lp/mm (20/40 VA level) and their Modulation Transfer Functions (MTFs) at the circle of least confusion. The MTFs define the resultant image quality at the best focus defined by the position of circle of least confusion.

To analyze depth-of-focus and image quality for 10 degrees of meridional misalignment between corneal toric lens and toric IOL, the principle meridian of the corneal lens was placed at 40 degrees orientation and the principle meridian of the toric IOL was placed at 50 degrees orientation. Again, Zemax optical design software was used to calculate corresponding TFRs and MTFs (FIGS. 8A and 8B) by the method described above for 5 degrees of meridional misalignment.

Tangential focal segment is referenced by the letter T and sagittal by the letter S in the figures. A distance between tangential and sagittal peaks increase with the meridional misalignment thus reducing their overlap and therefore, reducing the image quality at the best focus position defined by the position of the circle of least confusion.

FIGS. 7A and 7B demonstrate depth-of-foci of resultant tangential and sagittal focal segments in nominal astigmatism eye at 5 and 10 degrees meridional misalignments of contra-aspheric toric lens per FIG. 4.

To analyze depth-of-focus in terms of TFRs and image quality in terms of MTFs for 5 and 10 degrees (FIGS. 8A and 8B) of meridional misalignments between corneal toric lens and toric IOL, the principle meridian of the corneal lens was placed according to the method used for spherical toric lens analysis per the description under the FIG. 6A.

Tangential focal segment is referenced by the letter T and sagittal by the letter S in the figures. A distance between tangential and sagittal peaks increase with the meridional misalignment similar to the specification with spherical toric IOL but contra-aspherization increases the width of tangential and sagittal TFRs thus increasing their overlap at the position of the circle of least confusion that defines the best focus position. The contra-aspherization shifts the width of each focal segments more towards the best focus position—in this case, positive LSA in the tangential plane directs more light beyond the tangential focal segment towards the position of the circle of least confusion thus increase its contribution at the best focus position; negative LSA in the sagittal plane directs more light towards the lens in front of the sagittal focal segment also towards the position of circle of least confusion thus also increasing its contribution at the best focus position. Together they improve the image at the best focus position in tangential and sagittal orientations at the best focus as compare with the spherical toric lens at the same meridional misalignment.

There is another advantage of the a contra-aspheric design of toric lens. In case of a defocus from the position of circle of least confusion located at the middle between tangential and sagittal focal segments, the difference in image quality between tangential and sagittal orientations doesn't increase as drastically as in case of the corresponding spherical toric lens where tangential and sagittal peak are much more pronounced and therefore a difference in image quality between tangential and sagittal orientations increases much more drastically. It means that for the same amount of eye astigmatism and meridional misalignment the impact of spherical refraction error on image quality is much higher with spherical toric IOL than with contra-aspheric toric IOL.

FIGS. 8A and 8B demonstrate the examples of Modulation Transfer Functions (MTFs) of nominal astigmatic eye with spherical toric lens and contra-aspheric toric lens per FIG. 4 in aligned condition and 10 degrees meridional misalignment condition at the position of circle of least confusion. The method of calculation of the MTFs has been described under the FIG. 6A.

At best focus position defined by the position of the circle of least confusion, both tangential and sagittal MTFs of the eye with each toric IOL at different meridional misalignment are practically equivalent.

At the condition of a perfect alignment the MTF (T and S) of the eye with spherical toric IOL if better that the MTF (T and S) of the eye with contra-aspheric toric IOL but contra-aspheric toric lens still provides high quality MTF that highly unlikely may impact the image quality.

The MTF (T and S) of the eye with spherical toric IOL is substantially reduced in the case of 10 degrees meridional misalignment that the image quality can only reach about 20/40 of Visual Acuity (50 lp/mm of spatial frequency). The MTF (T and S) of eye with contra-aspheric toric IOL, on the other hand, is substantially higher and the image quality still reaches 20/20 of Visual Acuity (100 lp/mm of spatial frequency).

Figure 9:
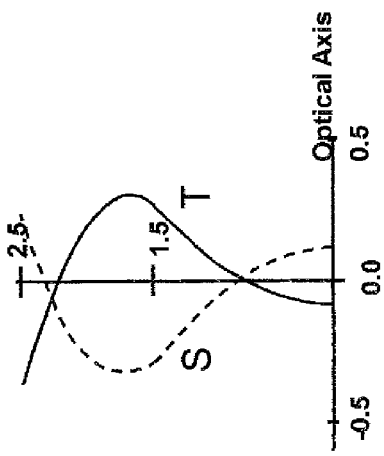
FIG. 9 illustrates an example of longitudinal spherical aberrations at y- and x-axes within 5 mm diameter of nominal astigmatic eye with 2.5 D cylinder corrected by contra-aspheric toric lens of opposite LSA signs at about 3 mm diameter region and within annulus of about 3 mm and 5 mm diameters where regions of each principle meridian includes the corresponding regional LSAs of opposite signs.

FIG. 9 demonstrate shapes of LSAs of the eye in y- and x-axes coinciding with the principle meridians of a toric surface, not only within 3 mm diameter but at 5 mm diameter that is important for scotopic condition of low illuminance and where the surface profile along each principle meridian takes bi-sign asphericity.

Both LSA shapes take a configurations of a bi-sign aspheric where each tangential LSA or sagittal LSA includes the LSA regions of one sign within about 3 mm diameter and the opposite sign outside about 3 mm diameter in order to include aberration compensation at large pupils.

In terms of general specification, the shape of one of the principle meridians comprises non-spherical profile with at least two regions within optical zone and one of these two regions being configured to produce a longitudinal ray aberration of a different sign the one produced by the other region.

A description of a bi-sign lens and its benefits were provided in the U.S. patent application Ser. No. 12/415,742;

"Bi-sign Aspheric Intraocular Lens", filed on Mar. 31, 2009. The contra-aspheric toric lens with LSAs of the eye model depicted on the FIG. 9 meets the bi-sign aspheric lens description as applied to a toric lens and thus is designed to improve image quality at large pupils as compare with a spherical toric lens of similar power.

The same specification is defined for base surface of a toric multifocal diffractive surface.

Figure 10:
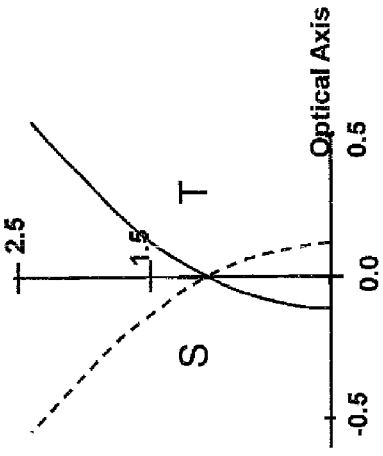
FIG. 10 illustrates an example of longitudinal spherical aberrations at y- and x-axes within 5 mm diameter of nominal astigmatic eye with 2.5 D cylinder corrected by contra-aspheric toric lens of opposite LSA signs at about 3 mm diameter region and within annulus of about 3 mm and 5 mm diameters where LSA of the same sign is maintained at both principle meridians.

FIG. 10 demonstrate shapes of LSAs of the eye in y- and x-axes coinciding with the principle meridians of a toric surface, not only within 3 mm diameter but at 5 mm diameter that is important for scotopic condition of low illuminance and where the surface profile along each principle meridian takes one-sign asphericity.

Both LSA shapes take a configurations of a one-sign aspheric where each tangential LSA and sagittal LSA includes the LSA regions of the same sign within about 3 mm diameter and outside about 3 mm diameter in order to include aberration compensation at large pupils.

The same specification is defined for base surface of a toric multifocal diffractive surface.

Figure 11:
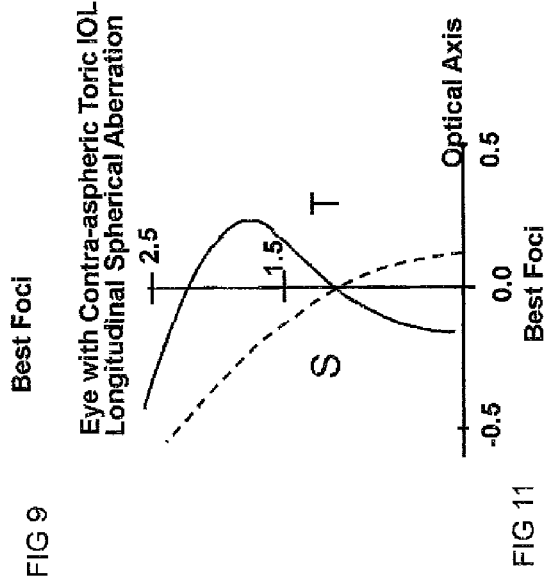
FIG. 11 illustrates an example of longitudinal spherical aberrations at y- and x-axes within 5 mm diameter of nominal astigmatic eye with 2.5 D cylinder corrected by contra-aspheric toric lens of opposite LSA signs at about 3 mm diameter region and the same signs within annulus of about 3 mm and 5 mm diameters.

FIG. 11 demonstrate shapes of LSAs of the eye in y- and x-axes coinciding with the principle meridians of a toric surface, not only within 3 mm diameter but at 5 mm diameter that is important for scotopic condition of low illuminance and where the surface profile along sagittal principle meridian takes one-sign asphericity and tangential—bi-sign asphericity.

Tangential LSA and sagittal LSA shapes are opposite signs within about 3 mm diameter and the same signs outside about 3 mm diameter.

A selection which asphericity belongs to tangential and sagittal orientation is arbitrary and determined by lens orientation.

The same specification is defined for base surface of a toric multifocal diffractive surface.

Figure 12:
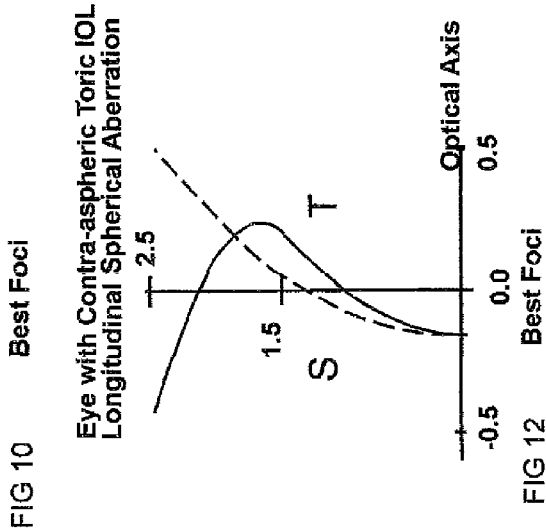
FIG. 12 illustrates an example of longitudinal spherical aberrations at y- and x-axes within 5 mm diameter of nominal astigmatic eye with 2.5 D cylinder corrected by contra-aspheric toric lens of the same signs of LSA at about 3 mm diameter region and opposite signs of LSA within annulus of about 3 mm and 5 mm diameters.

FIG. 12 demonstrate shapes of LSAs of the eye in y- and x-axes coinciding with the principle meridians of a toric surface, not only within 3 mm diameter but at 5 mm diameter that is important for scotopic condition of low illuminance and where the surface profile along sagittal principle meridians takes one-sign asphericity and tangential—bi-sign asphericity.

Tangential LSA and sagittal LSA shapes are the sane signs within about 3 mm diameter and opposite signs outside about 3 mm diameter.

A selection which asphericity belongs to tangential and sagittal orientation is arbitrary and determined by lens orientation.

The same specification is defined for base surface of a toric multifocal diffractive surface.

Although there has been hereinabove described a specific contra-aspheric toric ophthalmic lens in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An ophthalmic toric lens to be worn on an eye or implanted inside of an eye, the lens comprising:
    an anterior surface;
    a posterior surface; and
    a toric shape formed into one of the anterior and posterior surfaces, said toric shape comprising two non-spherical principle meridians each having a region within an annular area within about 3 mm diameter of optical zone wherein a region of a first principle meridian is flattened towards a lens periphery as compared to a corresponding first reference spherical surface and wherein a region of a second principle meridian is steepened towards the lens periphery as compared to a corresponding second reference spherical surface, wherein the first principle meridian is configured for producing a first longitudinal ray aberration of a different sign as compared to a second longitudinal ray aberration sign from the second principle meridian.

2. The lens according to claim 1 wherein the anterior and posterior surfaces are disposed on a contact lens.

3. The lens according to claim 1 wherein the anterior and posterior surfaces are disposed on an intraocular lens.

4. The lens according to claim 1 wherein the anterior and posterior surfaces are disposed on a corneal implant.

5. An ophthalmic toric lens to be worn on an eye or implanted inside of an eye, the lens comprising:
    an anterior surface;
    a posterior surface; and
    a toric shape formed into one of the anterior and posterior surfaces, said toric shape comprising two non-spherical principle meridians each having a region within an annular area of optical zone, wherein the curvature of the first principle meridian is flattened towards a lens periphery as compared to a corresponding first reference spherical surface where the first principle meridian and corresponding first reference spherical surface share a first common vertex radius and wherein the curvature of the second principle meridian is steepened towards the lens periphery as compared to a corresponding second reference spherical surface where the second principle meridian and corresponding second reference spherical surface share a second common vertex radius;
    wherein the first principle meridian is configured to produce a first longitudinal ray aberration of a different sign as compared to a second longitudinal ray aberration produced by the second principle meridian.

6. An ophthalmic toric lens to be worn on an eye or implanted inside of an eye, the lens comprising:
    an anterior surface;
    a posterior surface; and
    a toric shape formed into one of the anterior and posterior surfaces, said toric shape comprising two non-spherical principle meridians each having a region within an annular area of optical zone;
    wherein the curvature of the first principle meridian is flattened towards a lens periphery as compared to a corresponding first reference spherical surface, where the first principle meridian and corresponding first reference spherical surface share a first vertex radius; and
    wherein the curvature of the second principle meridian is steepened towards the lens periphery as compared to the corresponding second reference spherical surface, where the second principle meridian and corresponding second reference spherical surface share a second vertex radius.

\* \* \* \* \*